United States Patent
Hellberg

(10) Patent No.: US 7,288,510 B2
(45) Date of Patent: Oct. 30, 2007

(54) NITROGEN-CONTAINING ORTHO ESTER-BASED SURFACTANT, ITS PREPARATION AND USE

(75) Inventor: Per-Erik Hellberg, Svenshögen (SE)

(73) Assignee: Akzo Nobel N.V., Arnhem (NL)

( * ) Notice: Subject to any disclaimer, the term of this patent is extended or adjusted under 35 U.S.C. 154(b) by 495 days.

(21) Appl. No.: 10/487,972

(22) PCT Filed: Aug. 22, 2002

(86) PCT No.: PCT/SE02/01492

§ 371 (c)(1),
(2), (4) Date: Feb. 20, 2004

(87) PCT Pub. No.: WO03/018534

PCT Pub. Date: Mar. 6, 2003

(65) Prior Publication Data

US 2004/0198631 A1   Oct. 7, 2004

(30) Foreign Application Priority Data

Aug. 23, 2001  (SE) .................................. 0102799

(51) Int. Cl.
C11D 1/62   (2006.01)

(52) U.S. Cl. ...................... 510/329; 510/123; 510/124; 510/330; 510/341; 510/504

(58) Field of Classification Search ................. 510/123, 510/124, 329, 330, 341, 504
See application file for complete search history.

(56) References Cited

U.S. PATENT DOCUMENTS

| | | | |
|---|---|---|---|
| 3,786,029 A | 1/1974 | Bechara et al. | 260/75 |
| 3,879,465 A | 4/1975 | Bechara et al. | 260/584 C |
| 5,505,866 A | 4/1996 | Bacon et al. | 252/8.6 |
| 5,660,759 A * | 8/1997 | Segura et al. | 252/8.57 |
| 5,880,086 A | 3/1999 | Weinelt et al. | 510/504 |
| 6,897,196 B1 * | 5/2005 | Szoka et al. | 514/1 |

FOREIGN PATENT DOCUMENTS

| | | | |
|---|---|---|---|
| EP | 239910 | * | 10/1987 |
| EP | 0239910 B1 | | 10/1987 |
| EP | 409502 | * | 1/1991 |
| EP | 0409502 A2 | | 1/1991 |
| EP | 0409502 B1 | | 1/1991 |
| EP | 0564402 A1 | | 10/1993 |
| EP | 691396 | * | 5/1995 |
| EP | 0691396 A2 | | 1/1996 |
| GB | 2179364 A | | 3/1987 |
| WO | WO 99/32424 | | 7/1999 |

OTHER PUBLICATIONS

International Search Report, No. PCT/EP 02/01492, Nov. 27, 2002 (International Search Report, No. PCT/EP 02/01492, Nov. 27, 2002).
"Low-foaming nonionic surfactants containing ortho ester end groups," Juerg Haase et al.; Abstract of European Patent Application 0564402 A1; Oct. 6, 1993.
"Cationic Surfactants," Kurt Kosswig; Ullmann's Encyclopedia of Industrial Chemistry; Article Online Posting Date Jun. 15, 2000; pp. 1-5.
"Studies on the adsorption of non-ionic surfactants and the dripping behavior of their solutions by the drop volume and maximum bubble pressure technique," U. Teipel et al.; Physical Chemistry; 2000; pp. 297-308.
"Electrolytic Properties of Solutions of Paraffin-chain Quaternary Ammonium Salts," Allen B. Scott et al.; vol. 55; 1989; pp. 692-697.
"Physico-Chemical Properties Of Selected Anionic, Cationic And Nonionic Surfactants," N.M. van Os et al.; 1993; pp. 110-117, 1369.

* cited by examiner

Primary Examiner—Charles Boyer
(74) Attorney, Agent, or Firm—Ralph J. Mancini

(57) ABSTRACT

The present invention relates to a new tertiary or quaternary nitrogen-containing ortho ester-based surfactant, where the hydrophobic and hydrophilic parts am attached by separate ortho ester linkages. The ortho ester surfactants are stable in alkaline solutions, but are readily hydrolysed in acidic solutions. Since the hydrophobic and the hydrophilic parts of the surfactants reside in different substituents of the ortho ester, the surface activity is lost upon dydrolysis. The invention also relates to a process for making the ortho ester-based surfactants, where low molecular weight ortho esters are used as starting materials. These low molecular weight ortho esters are reacted with a hydrophobic component, which is an alcohol or an alkoxylated alcohol, and hydrophilic component, which is an alkanolamine or an alkoxylated alkanolamine. The molar amounts of the reactants are preferably 1-2 moles of the hydrophilic component per mole orthoester and 1-2 moles of the hydrophobic component per mole ortho ester. By this process surface active amino ortho esters are obtained. To obtain quaternary ammnonium ortho esters, the amnino ortho esters are reacted with an alkylating reagent such as methyl chloride or dimethyl sulphate. The nitrogen-containing ortho esters are surface active and form micelles, they are efficient in lowering the surface tension and have excellent wetting properties. They are suitable to be used in all applications where quaternary ammonium surfactants and tertiary amine surfactants are typically used.

12 Claims, No Drawings

NITROGEN-CONTAINING ORTHO ESTER-BASED SURFACTANT, ITS PREPARATION AND USE

The present invention relates to a new tertiary or quaternary nitrogen-containing ortho ester-based surfactant, where the hydrophobic and hydrophilic parts are attached by separate ortho ester linkages. The surfactants are stable in alkaline solutions, but are readily hydrolysed in acidic solutions to yield products that are not surface active.

Surfactants are used in a variety of applications and processes, but once their task is fulfilled their presence is often undesirable. From an environmental point of view, it is a great advantage if products that ultimately end up in the environment are easily degradable, either biologically or by other means. Quaternary ammonium surfactants have been used for e.g. fabric softening in domestic use, where the products ultimately will end up in a sewage plant or in natural waters. Many of these products are relatively toxic, and they have therefore to a great extent been replaced by fatty ester based quaternary ammonium compounds that are more environmentally friendly, the so-called esterquats. The latter are relatively stable in acid solution, but are readily hydrolysed at an alkaline pH. For a description of different quaternary ammonium compounds see Chapter 8 in the electronic version of Ullmann's Encyclopedia of Industrial Chemistry, year 2001 Wiley-VCH Verlag GmbH, Weinheim, Germany. See also e.g. EP-B1-239 910, EP-B1-409 502 and U.S. Pat. No. 5,505,866 for patents within this area.

Further, quaternary ammonium surfactants generally are poor wetters and the compounds exhibiting the highest surface activity normally have poor water solubility.

In order to improve the degradability of surfactants and make the separation of hydrophobic material from waste water easier, it has been suggested in WO 99/32424 to use hydrolysable ortho ester-based nonionic surfactants. The surfactants are stable in alkaline solutions but are hydrolysed in acidic solutions.

Ortho ester surfactants have been described in EP-A1-564 402, where an ortho ester group is used for end-capping of nonionic and cationic surfactants. The surfactants to be end-capped could be for example $C_8$-$C_{26}$ alcohol alkoxylates, $C_8$-$C_{26}$ fatty amine alkoxylates or a quaternised fatty amine alkoxylate. The products obtained are low-foaming, and can be used e.g. in machine dish-washing and bottle-cleaning. These products, however, will only marginally benefit from a better degradation, since a hydrolysis step will produce compounds that are still surface active.

In U.S. Pat. No. 3,879,465 and U.S. Pat. No. 3,786,029 ortho esters containing amino substituents are disclosed. These amino ortho esters are for example prepared from amino alkanols and ortho esters by transesterification of the alkoxy groups of the ortho ester wholly or partially by the amino alkanol. The products are claimed to have utility as activators in polyurethane formation.

The aim of the present invention is to provide nitrogen-containing surfactants, such as quaternary ammonium surfactants and tertiary amine surfactants, that will display good surfactant properties, such as wetting, and function well in all applications where nitrogen-containing surfactants typically are used, and which in addition are readily cleavable and more easily biodegradable than conventional quaternary ammonium and amine surfactants. Their degradation products should also be environmentally friendly, and not exhibit any essential surface activity. Further, this new kind of surfactants should be easy to produce. Surprisingly, it has now been found that nitrogen-containing surfactants based on an ortho ester that contains at least one substituent including a tertiary or quaternary nitrogen-containing group free from hydrocarbyl groups with 5 or more carbon atoms, and at least one substituent including a hydrophobic group with the formula $(A_1)_{n1}R_1$ where $R_1$ is a hydrocarbyl group with 5-22 carbon atoms, $A_1$ is an alkyleneoxy group with 3-4 carbon atoms and $n_1$ is a number between 0-30, display the above-mentioned properties.

Preferred ortho ester surfactants according to the invention are those having the formula

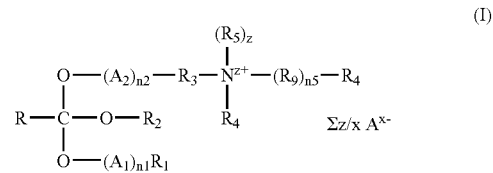

(I)

where R is hydrogen or an aliphatic group with 1-7 carbon atoms; $R_1$ is an aliphatic group with 5-22 carbon atoms, preferably 8-22; $A_1$ is an alkyleneoxy group with 3-4 carbon atoms; $A_2$ is an alkyleneoxy group with 2-3 carbon atoms where at least 50% of the alkyleneoxy groups are ethyleneoxy groups; $n_1$ is a number between 0 and 30, preferably between 0-20, provided that when $R_1$ is an aliphatic group with 5-6 carbon atoms $n_1$ is at least 1, preferably at least 2; $n_2$ is a number between 0 and 30, preferably 0-20; $R_3$ is an alkylene group with 1-4 carbon atoms, preferably 2-3; z is 0 or 1 and Σz is 0-4, preferably 1-2 and most preferably 1; $n_5$ is a number 0-1; $R_5$ is an alkyl group with 1-2 carbon atoms, preferably 1, or a group $(C_2H_4O)_sH$, where s is 1-10, preferably 1; $R_4$ is an alkyl group with 1-2 carbon atoms, preferably 1, a group $(C_2H_4O)_sH$, where s is 1-10, preferably 1, or the group $$(CH_2)_{n4} - \overset{(R_5)_z}{\underset{R_8}{N^{z+}}} - R_8$$

where $n_4$ is a number between 1 and 4, preferably 2-3, and $R_8$ is an alkyl group with 1-2 carbon atoms or a group $(C_2H_4O)_sH$, where s is 1-10, preferably 1; and $R_5$ and z have the same meaning as above; $R_9$ is a group $$(CH_2)_{n4} - \overset{(R_5)_z}{\underset{R_8}{N^{z+}}}$$

where $R_5$, $R_8$, z and $n_4$ have the same meaning as above; or the whole group $$\overset{(R_5)_z}{\underset{R_4}{N^{z+}}} - (R_9)_{n5} - R_4$$

in formula I represents the group

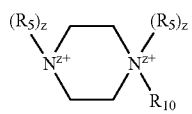

where $R_{10}$ is an alkyl group with 1-2 carbon atoms or a group $(C_2H_4O)_sH$, where s is 1-10, preferably 1; and $R_5$ and z have the same meaning as above; $R_2$ is selected from the group consisting of —$(A_1)_{n1}R_1$, —$(A_2)_{n2}$—$R_3$—$N^{z+}(R_4)(R_5)_z(R_9)_{n5}$—$R_4$, an alkyl group with 1-6 carbon atoms, preferably 1-4, and —$(A_3)_{n3}R_6$ where $A_3$ is an alkyleneoxy group with 2-3 carbon atoms and at least 50% of the alkyleneoxy groups are ethyleneoxy groups, $n_3$ is a number between 0-30 and $R_6$ is an alkyl group with 1-4 carbon atoms; $A_1$, $A_2$, $n_1$, $n_2$, $n_5$, $R_1$, $R_3$, $R_4$, $R_5$ and $R_9$ have the same meaning as mentioned above and $A^{x-}$ is an anion, where x is the charge of the anion; or a di- or polycondensate via any of the free hydroxy groups of the ortho ester. The number of nitrogen atoms in the nitrogen-containing substituents is preferably 1-2, most preferably 1. The symbol z+ denotes the charge of each individual nitrogen atom. When z is 1, the charge of the nitrogen atom in question is +1, and when z is zero the nitrogen atom is uncharged. The nitrogen atoms that are charged are quaternary and the uncharged nitrogen atoms are tertiary. Preferably only one of the nitrogen atoms per substituent is charged. Formula I represents an average ortho ester mixture, where specific individual species may have a structure deviating from formula I, since the substituents are randomly distributed. This fact is further exemplified and discussed later in the specification.

The ortho esters of formula I are surface active and form micelles, and they have excellent wetting properties. They are much more efficient in lowering the surface tension than monoalkyltrimethylammonium compounds based on fatty amines, and their good wetting properties are indicated by their low contact angle values as compared to the same references. Their foaming behaviour varies depending on the substituents, and it could be adapted to suit different applications. They are comparable or better hydrotropes than the conventional types, such as sodium cumene sulphonate or disodium octyliminodipropionate.

Since the hydrophobic and the hydrophilic parts of the surfactants reside in different substituents of the ortho ester, the surface activity is lost upon hydrolysis. The rapid cleavability of the ortho esters of the present invention presents a special advantage in application areas where the activity of the nitrogen-containing ortho ester is not desirable after its task has been fulfilled. An example of the latter is in the area of disinfection. The time needed for full antimicrobial effect to be exerted by a disinfectant is generally short. It is neither necessary nor desirable for the toxic compound to remain active after the disinfection has been achieved, since there is a risk for resistance development by harmful organisms. Consequently, the use of a temporary disinfectant would be beneficial. Quaternary ammonium ortho esters may also be used in the area of wood preservation, where a suitable application is for the temporary protection of freshly sawn timber against attack of sapstain fungi on the wood surface.

Other areas that are suitable are as rheology additives (e.g. for hard surface cleaning formulations) or together with organophilic clays for use as rheology modifiers in non-aqueous systems (oil/w-emulsions in paints, cosmetics and drilling muds), in viscose processing, and in fibre and textile processes such as dyeing and scouring. The quaternary ammonium ortho esters could also find use as antistatic agents, as softeners, as flotation agents, as anti-caking agents, as emulsion-breakers, as adjuvants or active compounds in agrochemical formulations for e.g. plant protection, as hydrotropes for other surfactants such as nonionic surfactants, in paper chemistry e.g. as a compound in wet strength additives or as debonding agents for cellulose pulp to be used in the production of fluff, as chain lubricants, as corrosion inhibitors, in soil remediation and in personal care products as e.g. releasing agents, conditioners and rheology additives.

Amino ortho esters that have not been quaternised could suitably be used as adjuvants in agrochemical formulations, in viscose processing, and in fibre and textile processes such as dyeing, scouring and to reduce roller build-up in hydrophobation processes. They could also find use as antistatic agents in polymers such as poly-olefins (e.g. polypropylene and polyethylene), as demulsifiers in fermentation processes, as corrosion inhibitors (e.g. for cooling water or in oilfield formulations), as flotation agents, as biocides in anti-microbial formulations, and in pigment processing e.g. to produce printing inks.

Also in sewage plants the temporary disinfectant properties are of value, since there is a smaller risk that the biodegrading organisms would be harmed when this kind of disinfectant is used. This is of particular value for applications where the quaternary ammonium compounds invariably end up in a water recipient, such as for softeners used in detergent formulations.

The cleavage of the ortho ester-based surfactant is promoted to a high degree by decreasing the pH and increasing the temperature. In that respect they are complementary to the so-called ester-quats, since these are relatively stable at an acid pH but not at an alkaline pH. The ortho ester could also be used at a lower pH, e.g. at a pH of 5, if the process is fast enough, and consequently be cleaved at the same pH. The cleavage results in degradation products that lack the ability to behave as surfactants, e.g. to lower the surface tension, which is demonstrated in Table 6 and 7 in Example 10.

The invention also relates to a process for making the ortho ester-based surfactants, where low molecular weight ortho esters are used as starting materials. These low molecular weight ortho esters are reacted with a hydrophobic component, which is an alcohol or an alkoxylated alcohol, and a hydrophilic component, which is an alkanolamine or an alkoxylated alkanolamine. The molar amounts of the reactants are preferably 1-2 moles of the hydrophilic component per mole orthoester and 1-2 moles of the hydrophobic component per mole ortho ester.

By this process surface active ortho esters containing one or more amino groups are obtained, where the hydrophobic and hydrophilic parts each individually is connected by ortho ester bonds to the molecule. To obtain quaternary ammonium ortho esters, the amino ortho esters are reacted with an alkylating reagent such as methyl chloride or dimethyl sulphate.

In more detail, the invention relates to a process where a tertiary amino ortho ester is prepared by reacting a trialkyl ortho ester, where the alkyl groups contain 1-6 carbon atoms, in one or several steps, with a hydroxyl-containing tertiary amine free from hydrocarbyl groups with 5 or more carbon atoms, and with a hydroxyl compound including a hydrophobic group with the formula $R_1(A_1)_{n1}$, where $R_1$, $A_1$ and $n_1$ have the meaning mentioned above, while evaporating alcohols derived from the alkyl groups of the ortho ester, and a quaternary ammonium ortho ester is prepared by further reacting the tertiary amino ortho ester obtained with an alkylating agent.

The preferred nitrogen-containing ortho ester-based surfactants of formula I can be produced by reacting an ortho ester of the general formula

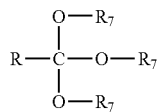

where R has the same meaning as in Formula I and $R_7$ is an alkyl group with 1-6 carbon atoms, preferably 1-4, in one or several steps, with reactants having the formulas HO—$(A_{1'})_{n1}$-$R_1$, HO—$(A_2)_{n2}$—$R_3$—N$(R_4)(R_9)_{n5}$—$R_4$ and, if so required, HO—$(A_3)_{n3}$-$R_6$ where $R_1$, $R_3$, $R_4$, $R_6$, $R_9$, $A_1$, $A_2$, $A_3$, $n_1$, $n_2$, $n_3$ and $n_5$ have the same meaning as in Formula I, while evaporating alcohols with the formula $R_7$OH, where $R_7$ has the same meaning as above. The reaction preferably is performed in the presence of an acid, e.g. methanesulphonic acid, p-toluenesulphonic acid or citric acid. The temperature is increased during the reaction and is finally reaching 100 to 160° C. The alcohols $R_7$OH, that are liberated during the reaction, are gradually evaporated from the reaction mixture. In the final phase of the reaction vacuum is applied to remove the residual amounts of liberated alcohols, thereby driving the reaction to completion. The resulting amino ortho ester has the formula III

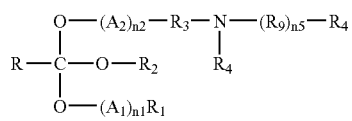

where R, $R_1$, $R_2$, $R_3$, $R_4$, $R_9$, $A_1$, $A_2$, $n_1$, $n_2$ and $n_5$ have the same meaning as in Formula I.

The surface active compound III may be used as such for certain applications.

Suitable examples of ortho esters II are methyl or ethyl ortho formate, methyl or ethyl ortho acetate and other low molecular weight ortho esters that are commercially available.

The hydrophobic part of the molecule may be derived from an alcohol $R_1$OH, or an alkoxylate thereof. The alcohol could either be synthetic or natural. Suitable examples of alkyl groups $R_1$ are 2-ethylhexyl, 2-propylheptyl, octyl, decyl, coco alkyl, lauryl, oleyl, rape seed alkyl and tallow alkyl. Other suitable hydrocarbon groups $R_1$ are those obtained from oxoalcohols, Guerbet alcohols, and methyl substituted alcohols with 2-4 groups having the formula —CH(CH$_3$)— included in the alkyl chain. The alcohols may also be propoxylated or butoxylated. The hydrophilic part of the molecule is preferably derived from an alkanolamine or an alkoxylated, preferably ethoxylated, alkanolamine. Suitable examples of alkanolamines are N,N-dimethylethanolamine, N,N-diethylethanolamine, N,N-dimethyldiglycolamine, N-methyldiethanolamine, N-methyl-hydroxyethylpiperazine, 1,4-bis(2-hydroxyethyl)piperazine, N,N-dimethyl-N',N'-bis(2-hydroxyethyl)propylenediamine, N,N-diethyl-N',N'-bis(2-hydroxyethyl)propylenediamine, 2-{[2-(dimethylamino)-ethyl]methylamino}ethanol, 3-dimethylamino-1-propanol, 3-diethylamino-1-propanol and triethanolamine. The hydrophilic part of the molecule could be further enhanced by also adding to the reaction mixture an alkyl blocked alkoxylate, suitably an ethoxylate where the blocking alkyl group contains 1-4 carbon atoms, preferably 1-2 carbon atoms.

The product resulting from the reaction described above is a mixture of several components. For each orthoester molecule there are three positions that could be substituted by the reactants. Consequently there will be some molecules with one amine-containing and one hydrophobic alcohol-containing substituent, some with two amine-containing and one alcohol-containing substituent and some with two alcohol-containing and one amine-containing substituent. These molecules are the most surface active ones. There will also be some amounts of material that is less surface active, because all three substituents are either amine-containing or alcohol-containing. The product mixture will be even more complex if also an alkyl-blocked alkoxylate has been added as a reactant. Thus a suitable embodiment of the invention is an ortho ester surfactant that contains 1-2 substituents that include a tertiary or quaternary nitrogen-containing group free from hydrocarbyl groups with 5 or more carbon atoms, 1-2 substituents that include a hydrophobic group with the formula $(A_1)_{n1}R_1$ where $R_1$ is a hydrocarbyl group with 5-22 carbon atoms, $A_1$ is an alkyleneoxy group with 3-4 carbon atoms and $n_1$ is a number between 0-30, and 0-1 substituents, that include a non-ionic group different from $(A_1)_{n1}R_1$ and which is selected from the group consisting of an alkyl group with 1-6 carbon atoms and a hydrophilic alkyl blocked polyoxyalkylene group, preferably a polyoxyethylene group where the blocking alkyl group contains 1-4 carbon atoms; and where the sum of the above-mentioned substituents is 2-3, preferably 3.

A quaternary ammonium ortho ester of formula I is obtainable by adding an alkylating agent containing an alkyl group with 1-2 carbon atoms, preferably methyl chloride or dimethyl sulfate, to the amino ortho ester of formula III in the presence of a base, preferably a carbonate or a bicarbonate. The quaternary ammonium ortho ester may also be obtained by reacting the tertiary amine ortho ester with ethylene oxide in the presence of an acid, e.g. HCl or $H_2SO_4$. The alkylation reaction may be performed with or without a solvent, preferably in the presence of a solvent. Preferred solvents are low-boiling alcohols such as isopropanol or ethanol. Isopropanol is a preferred solvent.

The choice of hydrophobic and hydrophilic parts and the relative amounts of them will of course vary between different applications, to satisfy their demands for a specific property of the compound.

The surface active nitrogen-containing ortho ester is normally used at a pH of 9 or above, but could also be used down to a pH of ca 6. To hydrolyse the nitrogen-containing ortho ester, the pH of the solution, emulsion or dispersion is preferably reduced to between 4 and 6. If needed, the temperature may be raised, preferably to between 20 and 60° C. to further promote the cleavage. In some circumstances, when the pH is low enough, it might suffice to raise the temperature. The lower the pH and the higher the temperature, the faster the cleavage will occur. In most circumstances it might be more convenient to lower the pH further than to raise the temperature above ambient, since the latter will often require a large energy input. When subjected to a neutral or slightly acidic pH in a sewage-treatment plant, the nitrogen-containing ortho ester surfactants are cleaved to yield non-toxic substances that are essentially not surface active. These substances would be expected to be more easily biodegraded than an intact surface active molecule would be, and it is not likely that they would harm the microorganisms.

The present invention is further illustrated by the following Examples.

EXAMPLE 1

Production of Amino Ortho Ester (Step 1)

6 moles of triethyl orthoformate, 8.4 moles of N,N-dimethylethanolamine and 1.6 g of anhydrous citric acid were mixed at ambient temperature in a 2 l round-bottomed flask equipped with a short distillation column, condenser and vacuum outlet.

The temperature was then raised to 90° C. and a slight vacuum applied (950 mbar). After around 45 minutes, the transesterification reaction had started, and a stream mainly consisting of liberated ethanol was distilled off. Minor amounts of triethyl ortho formate and N,N-dimethyl ethanolamine were simultaneously removed. During the reaction, the temperature and vacuum were stepwise increased to 100° C. and 930 mbar, respectively. The reaction was followed by $^1$H— and $^{13}$C—NMR and stopped as a suitable degree of substitution was reached.

The following product distribution in the reaction mixture was estimated by the $^1$H—NMR analysis (see Table below). X denotes the number of ethoxy groups that has not been substituted, and z denotes the number of N,N-dimethyl aminoethyl groups.

| Component (mol %) | x | z |
|---|---|---|
| 19[1] | 3 | 0 |
| 47 | 2 | 1 |
| 28 | 1 | 2 |
| 6 | 0 | 3 |

[1]untreated triethyl orthoformate (all groups are ethoxy groups)

In addition, 20 mol % of the total number of N,N-dimethyl aminoethyl groups present are in the form of unreacted N,N-dimethylethanolamine.

Production of Amino Ortho Ester (Step 2)

To 150 g of this mixture, 0.75 moles of n-tetradecanol and 0.9 g of anhydrous citric acid was added. The temperature was set to 105° C. and the vacuum to 960 mbar. During the reaction, the temperature and vacuum were increased stepwise to 110° C. and 200 mbar, respectively. The reaction was followed by $^1$H— and $^{13}$C—NMR and stopped as a suitable degree of substitution was reached.

According to the NMR analysis more than 54 mol % of the product consists of the three surface active components specified below. The number of ethoxy groups that has not been substituted is denoted by x, the number of n-tetradecyl groups by y and the number of N,N-dimethyl aminoethyl groups by z.

| Component no | x | y | z |
|---|---|---|---|
| 1 | 1 | 1 | 1 |
| 2 | 0 | 2 | 1 |
| 3 | 0 | 1 | 2 |

In addition, around 10% of the total number of N,N-dimethyl aminoethyl groups present are in the form of unreacted N,N-dimethylethanolamine. The amount of free tetradecanol is just above the detection limit for 13C—NMR. No unreacted triethyl orthoformate was found.

The reaction to produce amino substituted ortho esters of the present invention can also be carried out as a one-pot synthesis as is demonstrated in Examples 3-7.

Quaternisation Step 249 g of the product from the reaction described above was mixed with 50 g isopropyl alcohol and 5 g NaHCO$_3$. This mixture was charged into a stirred autoclave, which was nitrogen purged, evacuated and heated to 85° C., and then 36.6 g (0.726 moles) methyl chloride was added stepwise. The reaction was followed by monitoring the pressure in the autoclave. After 5 h, the temperature was lowered to 30° C. and the autoclave evacuated again before the product was discharged.

To ascertain a long-term stability of the product, the pH (as measured for a 1% solution of the product in water) was raised from 7.7 to 10.6 by addition of 40 g of a 25% (w/w) solution of KOH in methanol.

Analysis by $^1$H—NMR and $^{13}$C—NMR showed that there was no remaining unreacted tertiary amine, and that the ortho ester links were intact.

EXAMPLE 2

The reaction product between triethyl orthoformate and N,N-dimethylethanolamine, as is described in Example 1 step 1, was used for the consecutive steps. To 200 g of this intermediate, 1.00 mole of 2-ethylhexanol and 0.4 g of anhydrous citric acid was added. The temperature was set to 105° C. and the vacuum to 960 mbar. During the reaction, the vacuum was stepwise increased to 200 mbar. The reaction was followed by $^1$H— and $^{13}$C—NMR and stopped as a suitable degree of substitution was reached. According to the NMR analysis more than 47% of the product consists of the three surface active components corresponding to the ones specified in the table of Example 1. The number of ethoxy groups that has not been substituted is denoted by x, the number of 2-ethylhexyl groups by y and the number of N,N-dimethylaminoethyl groups by z. No unreacted triethyl orthoformate, N,N-dimethylethanolamine or 2-ethylhexanol was found.

Quaternisation Step 178 g of the product from the reaction described above was mixed with 36 g isopropyl alcohol and 3.6 g NaHCO$_3$. This mixture was charged into a stirred autoclave, which was nitrogen purged, evacuated and heated to 85° C., and then 31.8 g (0.631 moles) methyl chloride was added stepwise. The reaction was followed by monitoring the pressure in the autoclave. After 4.5 h, the temperature was lowered to 30° C. and the autoclave evacuated again before the product was discharged.

To ascertain a long-term stability of the product, the pH (as measured for a 1% solution of the product in water) is raised from 7.8 to 10.5 by addition of 25 g of a 25% (w/w) solution of KOH in methanol.

Analysis by $^1$H—NMR and $^{13}$C—NMR showed that there was no remaining unreacted tertiary amine, and that the ortho ester links were intact.

The same procedure as described in Example 1 and 2 was used to synthesise the ortho ester-based quaternary ammonium compounds A-F, by reacting triethyl ortho formate, N,N-dimethyl ethanolamine and the respective alcohols displayed in the table below, and the resulting ortho ester amines were then quaternised. The conditions for the quaternisation step for the respective products are collected in Table 1.

By titration the amount of quaternised ortho ester was determined to be 1.49 meq/g, and for free tertiary amine the amount was 0.043 meq/g.

TABLE 1

| Example | Fatty alcohol | Amount of ortho ester amine (g) | Amount of isopropyl alcohol (g) | Amount of NaHCO$_3$ (g) | Amount of MeCl (g) | Time for quaternization (h) | Quaternary ammonium ortho ester[b] (meq/g) |
|---------|---------------|---------------------------------|---------------------------------|-------------------------|--------------------|------------------------------|---------------------------------------------|
| A | 2-Ethylhexanol | 178 | 36 | 3.6 | 32 | 4.5 | 1.43 |
| B | n-Octanol | 183 | 37 | 3.7 | 33 | 7 | 1.49 |
| C | n-Decanol | 203 | 41 | 4.1 | 34 | 6.5 | 1.58 |
| D | n-Dodecanol | 192 | 42 | 3.8 | 30 | 15[a] | 1.30 |
| E | n-Tetradecanol | 249 | 50 | 5.0 | 37 | 5 | 1.52 |
| F | n-Hexadecanol | 201 | 47 | 4.0 | 28 | 16[a] | 1.03 |

[a]the reactions were run over night
[b]determined by emulsion titration against sodium lauryl sulfate on vacuum treated product, i.e. IPA and MeOH is removed

EXAMPLE 3

0.5 moles of triethyl orthoformate, 0.7 moles of N,N-diethylethanolamine, 0.7 moles of dodecanol and 2.0 g of a strongly acidic ion-exchange resin (Amberlyst®15) were mixed at ambient temperature in a 500 ml round-bottomed flask equipped with a distillation column, condenser and vacuum outlet.

The temperature was then raised to 125° C. and a vacuum applied (450 mmHg). After around 40 minutes, the transesterification reaction had started, and a stream mainly consisting of liberated ethanol was distilled off. The contents of the distillate as well as of the product resulting from the transesterification reaction were continuously monitored by gas chromatography, revealing that the distillate contained >96.5% ethanol. The temperature and vacuum were continuously adjusted during the reaction to remove the residual amount of ethanol, thereby driving the reaction to completion. The maximum temperature was 160° C. and the minimum pressure was 90 mmHg. After a total reaction time of 7 h, the reaction was stopped, since a suitable degree of substitution had been reached according to gas chromatography. According to the GC analysis more than 60% of the product consists of the three surface active components corresponding to the ones specified in the table of Example 1. The number of ethoxy groups that has not been substituted is denoted by x, the number of C12 linear primary alkyl groups by y and the number of N,N-dimethyl aminoethyl groups by z. In addition, around 11% of the total number of N,N-dimethylaminoethyl groups present are in the form of unreacted N,N-dimethylethanolamine. The amount of free C12 linear primary alcohol is just above the detection limit for $^{13}$C—NMR. No unreacted triethyl orthoformate was found.

Quaternisation Step 182 g of the product from the reaction described above was mixed with 23 g isopropyl alcohol and 1.8 g NaHCO$_3$. This mixture was charged into a stirred autoclave, which was nitrogen purged, evacuated and heated to 95° C., and then 33.5 g (0.481 moles) of methyl chloride was added stepwise. The reaction was followed by monitoring the pressure in the autoclave.

After a total reaction time of 10 h the temperature was lowered to 30° C., and the autoclave was evacuated again before the product was discharged.

EXAMPLE 4

1.0 moles of triethyl orthoformate, 1.3 moles of 3-diethylamino-1-propanol, 1.3 moles of dodecanol and 7.5 g of the same catalyst as in example 3 were mixed at ambient temperature in a 1 l round-bottomed flask equipped with a distillation column, condenser and vacuum outlet.

The temperature was then raised to 120° C. and a vacuum applied (375 mmHg). After around 40 minutes, the transesterification reaction had started, and a stream mainly consisting of liberated ethanol was distilled off. The contents of the distillate as well as of the product resulting from the transesterification reaction were continuously monitored by gas chromatography, revealing that the distillate contained >96.5% ethanol, the rest mainly being triethyl orthoformate. The temperature and vacuum was continuously adjusted during the reaction to remove the residual amount of ethanol, thereby driving the reaction to completion. The maximum temperature was 160° C. and the minimum pressure was 100 mmHg. After a total reaction time of 7 h, the reaction was stopped, since a suitable degree of substitution had been reached according to gas chromatography.

According to the GC analysis more than 60% of the product consists of the three surface active components corresponding to the ones specified in the table of Example 1. The number of ethoxy groups that has not been substituted is denoted by x, the number of C12 linear primary alkyl groups by y and the number of N,N-diethyl aminopropyl groups by z. The amount of free C12 linear primary alcohol is just above the detection limit for $^{13}$C—NMR. No unreacted triethyl orthoformate was found.

Quaternisation Step

To 50.9 g of the product from the reaction described above, 19.2 g of dimethyl sulfate (DMS) was added under nitrogen at 40-70° C. during 20 minutes. This mixture was kept at 75-80° C. and under nitrogen for one hour to complete the reaction. According to $^{13}$C—NMR analysis 95% of the amine was quaternised.

EXAMPLE 5

0.5 moles of triethyl orthoformate, 0.65 moles of 2-{[2-(dimethylamino)ethyl]methylamino}ethanol, 0.65 moles of dodecanol and 3.0 g of the same catalyst as in example 3 were mixed at ambient temperature in a 500 ml round-bottomed flask equipped with a distillation column, condenser and vacuum outlet.

The temperature was then raised to 110° C. and a vacuum applied (375 mmHg), whereafter the transesterification reaction had started, and a stream mainly consisting of liberated ethanol (>95% by GC) was distilled off. The temperature and vacuum was continuously adjusted during the reaction to remove the residual amount of ethanol, thereby driving the reaction to completion. The maximum temperature was 160° C. and the minimum pressure was 90 mmHg.

When 85% of the theoretical amount of ethanol had been distilled off, an additional amount of 2.0 g of catalyst was added. After a total reaction time of 12 h the reaction was stopped, since the theoretical amount of ethanol had been distilled off.

According to the GC analysis more than 64% of the product consists-of the three surface active components corresponding to the ones specified in the table of Example 1. The number of ethoxy groups that has not been substituted is denoted by x, the number of C12 linear primary alkyl groups by y and the number of 2-{[2-(dimethylamino)ethyl]methylamino}ethyl groups by z. The amount of free C12 linear primary alcohol is just above the detection limit for $^{13}C$—NMR. No unreacted triethyl orthoformate was found.

Quaternisation Step

To 53.7 g of the product obtained by the reaction described above, 34.0 g of DMS was added under nitrogen at 60-75° C. during 50 minutes. When 75% of the DMS had been charged, 16 g of isopropyl alcohol was added to decrease the viscosity. After the remaining DMS had been added, the reaction mixture was kept at 75-80° C. and under nitrogen for one hour to complete the reaction. According to $^{13}C$—NMR analysis all amine had been quaternised.

EXAMPLE 6

1.80 moles of triethyl orthoformate, 1.80 moles of N-methyldiethanolamine, 2.53 moles of dodecanol and 0.7 g of anhydrous citric acid were mixed at ambient temperature in a 2 l round-bottomed flask equipped with a short distillation column, condenser and vacuum outlet.

The temperature was then raised to 110° C. and a slight vacuum applied (980 mbar). After around 45 minutes, the transesterification reaction had started, and a stream consisting of liberated ethanol was distilled off. The contents of the distillate as well as the product resulting from the transesterification reaction were continuously monitored by $^{1}H$— and $^{13}C$—NMR, revealing that the distillate mainly contained ethanol and a very small amount of triethyl orthoformate. After 25 h the reaction was stopped, since a suitable degree of substitution then had been reached according to $^{1}H$— and $^{13}C$—NMR.

A minor amount of free dodecanol was detected by $^{13}C$—NMR. No unreacted triethyl orthoformate was found.

Quaternisation Step 213 g of the product obtained from the reaction described above was mixed with 43 g isopropyl alcohol and 4 g NaHCO$_3$. This mixture was charged into a stirred autoclave, which was nitrogen purged, evacuated and heated to 85° C. and then 31.2 g (0.618 moles) of methyl chloride was added stepwise. The reaction was followed by monitoring the pressure in the autoclave.

After 6 h the temperature was lowered to 30° C., and the autoclave was evacuated again before the product was discharged.

To ascertain a long-term stability of the product, the pH (as measured for a 1% solution of the product in water) was raised from 7.8 to 11.3 by addition of 25 g of a 25% (w/w) solution of KOH in methanol.

Analysis by $^{1}H$—NMR and $^{13}C$—NMR showed that there was no remaining unreacted tertiary amine, and that the ortho ester links were intact. By emulsion titration against sodium lauryl sulfate, the amount of quaternised ortho ester was determined to be 1.34 meq/g.

EXAMPLE 7

0.56 moles of triethyl orthoformate, 0.79 moles of the addition product between N,N-dimethylethanolamine and 3 moles of ethylene oxide, 0.79 moles of dodecanol, 0.5 g of acetic acid and 0.7 g of anhydrous citric acid were mixed at ambient temperature in a 2 l round-bottomed flask equipped with a short distillation column, condenser and vacuum outlet.

The temperature was then raised to 110° C. and a slight vacuum applied (980 mbar). After 16 h 0.4 g of citric acid was added, and after 25 h the reaction was stopped, since a suitable degree of substitution then had been reached according to $^{1}H$— and $^{13}C$—NMR.

A minor amount of free dodecanol was detected by $^{13}C$—NMR. No unreacted triethyl orthoformate was found.

Quaternisation Step 159 g of the product obtained from the reaction described above was mixed with 32 g isopropyl alcohol and 3 g NaHCO$_3$. This mixture was charged in a stirred autoclave, which was nitrogen purged, evacuated and heated to 85° C., and 30.4 g of methyl chloride was added stepwise. The reaction was followed by monitoring the pressure in the autoclave.

After 6 h, the temperature was lowered to 30° C., and the autoclave was evacuated again before the product was discharged.

To ascertain a long-term stability of the product, the pH (as measured for a 1% solution of the product in water) was raised from ca 6 to 11.2 by addition of 33 g of a 25% (w/w) solution of KOH in methanol.

Analysis by $^{1}H$—NMR and $^{13}C$—NMR showed that there was no remaining unreacted tertiary amine, and that the ortho ester links were intact.

EXAMPLE 8

By determining the critical micelle concentration (cmc) and the surface tension at a concentration of 0.1% (1 g/l), the products in Table 2 were shown to have the basic surface chemical properties necessary to work as efficient surfactants in various applications. As a comparison, the values for n-dodecyltrimethylammonium bromide and n-tetradecyltrimethylammonium bromide are included. From the Table it is obvious that the quaternary ammonium ortho ester mixtures of the invention are much better at lowering the surface tension than the quaternary ammonium compound references.

TABLE 2

| Product from example No | cmc at 21° C. (g/l) | γ at 0.10% and 21° C. (mN/m) | Surface age for γ at 0.10% (s) |
|---|---|---|---|
| A[a] | 0.4 | 29.8 | 7 |
| B[a] | 0.3 | 25.8 | 8 |
| C[a] | 0.1 | 23.8 | 6 |
| D[a] | 0.06 | 31.1 | 7 |
| E[a] | 0.08 | 24.5 (50° C.) | 8 |
| F[a] | 0.05 | 31.2 (50° C.) | 6 |
| 3[b] | 0.2 | 23 | — |

TABLE 2-continued

| Product from example No | cmc at 21° C. (g/l) | γ at 0.10% and 21° C. (mN/m) | Surface age for γ at 0.10% (s) |
|---|---|---|---|
| 4[b] | 0.1 | 24 | — |
| 5[b] | 0.7 | 24 | — |
| Dodecyltrimethyl-ammonium bromide[a] | 4.9[c] | 52.5 | 4 |
| Tetradecyltrimethyl-ammonium bromide[a] | 1.2[d] | 41.5 | 3 |

[a]The data were recorded in a pH 8 - buffer solution (P-H TAMM Laboratorier AB, Uppsala, Sweden). The cmc values were measuredusing the du Noüy ring and the surface tensions at 0.10% were recorded using a Sensadyne PC500-L Surface Tensiometer(Chem-Dyne Research Corp., Mesa, Az., United States) by the bubble pressure method (U. Teipel and N. Aksel, Tenside Surf. Det. 37 (2000)5, p. 297-308 and references therein). The surface tension for the pure buffer solution was 73.1 mN/m.
[b]The data were recorded in tap water, and the cmc and surface tension values at 0.10% were measured using the Wilhelmy plate.
[c]Literature value from Scott, A. B. and Tartar, H. V., Electrolytic Properties of Solutions of Paraffin-chain QuaternaryAmmonium Salts, J. Am. Chem. Soc. 65:692 (1943).
[d]Literature value from van Os, N. M., Haak, J. R. and Rupert, L. A. M., Physico-chemical Properties of Selected Anionic,Cationic and Nonionic Surfactants, ELSEVIER, Amsterdam-London-New York-Tokyo 1993.

EXAMPLE 9

The hydrolysis characteristics for some of the products earlier described were measured using a Mütek PCD 03 Particle Charge Detector (Mütek Analytic GmbH, Herrsching, Germany) for titration on cationic surfactant activity. The surfactants (the product mixtures obtained from the reactions specified in Table 1) were dissolved in buffer solutions with a pH of 3.0, 4.0 or 10.0 (Reagecon, Shannon, Ireland) to obtain a concentration of around 20 g/l, and the solutions were continuously stirred. Samples were withdrawn at suitable intervals, diluted and titrated against 0.00349 M sodium dodecylbenzene sulfonate.

The results in Tables 3-5 show that the surfactants even in concentrations high over the critical micelle concentration are readily hydrolysed under mild acidic conditions, at the same time as they are long-term stable in high-pH formulations. The hydrolysis rate is enhanced even further by a moderate increase in temperature.

TABLE 3

| Time (minutes) | Cationic surfactant activity measured at pH = 3.0, 21° C. (μeq/g) | |
|---|---|---|
|  | Surfactant C | Surfactant D |
| 2 | 6.5 | 9.0 |
| 21 | — | 3.8 |
| 81 | 2.8 | — |
| 84 | — | 1.7 |
| 142 | — | 0.6 |
| 165 | 0.6 | — |
| 216 | 0.1 | — |
| over night | — | <0.1 |

TABLE 4

| Time (minutes) | Cationic surfactant activity measured at pH = 4.0 (μeq/g) | | | |
|---|---|---|---|---|
|  | Surfactant C | | Surfactant D | |
|  | 21° C. | 50° C. | 21° C. | 50° C. |
| 2 | — | — | 15.2 | 9.6 |
| 3 | 15.2 | 11.2 | — | — |
| 14 | — | 7.0 | — | — |
| 39 | — | 3.7 | 6.4 | — |
| 45 | 9.0 | — | — | — |
| 52 | — | — | — | 1.4 |
| 95 | 6.8 | — | — | — |
| 108 | — | — | 3.7 | — |
| 122 | — | — | — | 0 |
| 180 | — | 0.8 | — | — |
| 345 | 2.7 | — | — | — |
| 355 | — | — | 1.8 | — |
| over night | 0 | — | 0.1 | — |

TABLE 5

| Time (days) | Cationic surfactant activity measured at pH = 10.0, 21° C. (μeq/g) Surfactant C |
|---|---|
| 4.5 hours | 18.3 |
| 1 | 18.6 |
| 3 | 18.9 |
| 6 | 18.8 |
| 13 | 18.9 |
| 62 | 19.6 |
| 160 | 18.9 |
| 261 | 18.4 |

EXAMPLE 10

The results in example 9 show the actual chemical hydrolysis of the quaternary ammonium ortho ester based surfactants, but from an applicational point of view, it is the disappearance of the surface chemical activity that is of interest. This often takes place at concentrations much higher than zero concentration of surfactant, as measured by e.g. titration. The actual concentration at which the surfactant can no longer carry out its task is naturally depending on the application (emulsification, disinfection etc.).

The hydrolysis characteristics for surfactant C, that was investigated in example 9 by titration of cationic activity, was in this example measured by studying the surface tension using a Sensadyne PC500-L Surface Tensiometer (Chem-Dyne Research Corp., Mesa, Ariz., United States) with the bubble pressure method (see reference in Example 8). Surfactant C was dissolved in buffer solutions (Reagecon, Shannon, Ireland) with various pH (around 1 g/l of the product mixture obtained from the reaction specified in Table 1) and the surface tension was measured as a function of time. The solutions were continuously stirred except during the measurements. With the method used, the surface tension is measured by creation of nitrogen bubbles in the bulk phase, thus avoiding the problem of hydrophobic material reaching the surface of the surfactant solution and disturbing the measurement as the hydrolysis of the surfactant proceeds. The results in Tables 6-7 display that the ready hydrolysis under the mild acidic conditions accounted for in example 9 also corresponds to a loss of the surface activity.

TABLE 6

| Time (minutes) | Surface Tension pH = 2.0, 21° C. (mN/m) | Surface Age of bubble (s) |
|---|---|---|
| 3.5 | 28.9 | 15 |
| 78 | 30.7 | 13 |
| 159 | 45.0 | 18 |
| 256 | 50.8 | 15 |
| 318 | 50.5 | 14 |

TABLE 7

| | pH = 3.0, 21° C. | | pH = 3.0, 50° C. | |
|---|---|---|---|---|
| Time (minutes) | Surface Tension (mN/m) | Surface Age (s) | Surface Tension (mN/m) | Surface Age (s) |
| 4 | 29.6 | 7 | — | — |
| 5 | — | — | 33.0 | 7 |
| 40 | 31.7 | 7 | 33.1 | 6 |
| 97 | — | — | 49.5 | 10 |
| 140 | 42.4 | 9 | — | — |
| 208 | 48.1 | 11 | — | — |
| 225 | — | — | 59.8 | 12 |
| 360 | — | — | 58.6 | 13 |
| 435 | 49.9 | 11 | — | — |

— test not performed

EXAMPLE 11

Good wetting properties of the surfactant is often a prerequisite for many of the earlier mentioned applications. Especially in alkaline solutions there is a need for good wetting agents. In this example, the wetting properties of alkaline formulations of some of the surfactants earlier described are tested by dynamic contact angle measurements.

TABLE 8

| Component | Formulation I % w/w of component | Formulation II % w/w of component | Formulation III % w/w of component |
|---|---|---|---|
| Surfactant A | 5 | — | — |
| Surfactant B | — | 5 | — |
| Surfactant C | — | — | 5 |
| Tetrasodium pyrophosphate | 3 | 3 | 3 |
| Sodium metasilicate x 5 H2O | 2 | 2 | 2 |
| Water (18 MΩ/cm) | balance | balance | balance |

Formulations I-III above were diluted 1:10 before measurements. The dynamic contact angle was measured on a hydrophobic, polymeric material (Parafilm PM-922, American Can Company) using a First Ten Ångstroms FTÅ 200 instrument (Portsmouth, Va., USA) equipped with a video camera and an image analyzing unit. The results are summarized in the table below.

TABLE 9

| | Contact angle (°) after | | |
|---|---|---|---|
| Formulation | 10 s | 30 s | 1 min |
| I | 34.3 | 30.9 | 30.1 |
| II | 41.9 | 35.2 | 32.0 |
| III | 51.5 | 43.7 | 36.3 |
| Dodecyltrimethyl-ammonium bromide[a] (Reference) | 68.2 | 67.9 | 67.4 |
| Tetradecyltrimethyl-ammonium bromide[b] (Reference) | 60.4 | 60.1 | 59.1 |

The references were formulated in the same way as the surfactants A, B and C.
[a]clear homogeneous solution
[b]opaque solution
Didodecyldimethylammonium bromide, which is a much more hydrophobic quaternary ammonium compound, was insoluble in this formulation.

The tested surfactants were thus found to have excellent wetting properties with low contact angles very rapidly after application of the formulation on the surface.

EXAMPLE 12

The new surfactants also have good properties as hydrotropes in different formulations for e.g. cleaning applications, which is demonstrated by the following experiment to determine the clarity interval for the formulation below.

TABLE 10

| Ingredient | % by weight |
|---|---|
| Tetrapotassium pyrophosphate | 6 |
| Sodium metasilicate pentahydrate | 4 |
| C$_9$—C$_{11}$-alcohol + 4EO (narrow range)[a] | 5 |
| Hydrotrope | X |
| Water | balance |

[a]C$_9$—C$_{11}$-alcohol with a linearity above 80% w/w that has been ethoxylated with 4 moles of ethylene oxide per mole alcohol in the presence of a narrow range catalyst.

Tetrapotassium pyrophoshate and sodium metasilicate pentahydrate were dissolved in tap water. The ethoxylated alcohol was added to this solution, which then turned cloudy. The hydrotrope was added until the solution was clear, and the required amount was recorded. Then the temperature was raised until the mixture went cloudy again. The results in the Table below show that the quaternary ammonium ortho esters are comparable or better hydrotropes than the commonly used hydrotropes disodium octyliminodipropoinate and sodium cumene sulfonate.

TABLE 11

| Hydrotrope compound | Active amount of hydro trope added % (w/w) | Cloud point of formulation (° C.) |
|---|---|---|
| Disodium octyliminodi-propionate (reference) | 6.0 | 45-50 |
| Sodium cumene sulfonate (reference) | 9.0 | 45-50 |
| Surfactant A | 7.0 | 52 |
| Surfactant B | 5.0 | 48 |

EXAMPLE 13

The foaming behaviour of the quaternary ammonium ortho esters B and D was compared to the foaming behaviour of n-dodecyl-trimethylammonium bromide (n-C12-TAB).

Method Description

The surfactant is dissolved in distilled water and diluted to a defined concentration. 500 ml of this solution is transferred to a thermostatable glass cylinder, graduated to 1500 ml. The solution is then circulated through a stainless steel tube using a pump. The solution enters the tube in the bottom of the glass cylinder and is released ca. 14 cm above the 1500-ml mark on the cylinder. The pump speed is 200 liter/h.

The solution is circulated for 10 minutes (foam level recorded each minute), the pump is then stopped, and the foam level recorded for additional 5 minutes (proposed ISO-method ISO 4877).

TABLE 12

|  | Foam Volume (ml) | | | | | | |
|---|---|---|---|---|---|---|---|
|  | Surfactant B | | |  |  | n-C12-TAB | |
| Time (min) | 0.01% | 0.1% | 0.1% acid treated* | Surfactant D 0.01% | n-C12-TAB 0.01% | n-C12-TAB 0.1% | 0.1% acid treated* |
| 1 | 120 | 700 | 140 | 140 | 160 | 780 | 820 |
| 2 | 120 | 1380 | 140 | 160 | 160 | 1080 | 1100 |
| 3 | 120 | >1500 | 140 | 160 | 160 | 1260 | 1280 |
| 4 | 120 | >1500 | 140 | 160 | 140 | 1340 | 1360 |
| 5 | 120 | >1500 | 140 | 160 | 140 | 1370 | 1380 |
| 6 | 120 | >1500 | 120 | 160 | 140 | 1360 | 1380 |
| 7 | 120 | >1500 | 120 | 160 | 140 | 1360 | 1360 |
| 8 | 120 | >1500 | 120 | 160 | 140 | 1340 | 1360 |
| 9 | 120 | >1500 | 120 | 160 | 140 | 1320 | 1350 |
| 10 | 120 | >1500 | 100 | 160 | 140 | 1320 | 1340 |
| 11 | 0 | >1500 | 0 | 100 | 0 | 1200 | 800 |
| 12 | 0 | >1500 | 0 | 100 | 0 | 800 | 340 |
| 13 | 0 | >1500 | 0 | 100 | 0 | 400 | 280 |
| 14 | 0 | >1500 | 0 | 100 | 0 | 260 | 120 |
| 15 | 0 | >1500 | 0 | 100 | 0 | 180 | 60 |

*pH of the solution is lowered to 2.5 using conc. sulfuric acid and the solution is then stirred for 10 minutes before the foam test is carried out.

In many applications it is desirable to use low foaming surfactants, while in others a high and stable foam is wanted, at least in some stage of the process where the surfactant is used.

As is shown in the Table above, the surfactants of this invention are low foaming at low concentrations, while they give a stable, large foam volume at higher concentrations. By short-term acid treatment the surfactants are hydrolysed, which is manifested by the much lower foam levels obtained from these solutions as compared with the untreated surfactant solutions. This may be very beneficial in processes where temporary foaming is desired. As a reference n-dodecyltrimethylammonium bromide (n-C12-TAB) is used, which is an example of a traditional stable quaternary ammonium compound. The reference is not affected by the addition of acid, and the foam volume generated by an acid treated sample is about the same as it is for a non-treated sample.

The invention claimed is:

1. An ortho ester surfactant, wherein at least one substituent includes a tertiary or quaternary nitrogen-containing group free from hydrocarbyl groups with 5 or more carbon atoms, and at least one substituent includes a hydrophobic group with the formula $(A_1)_{n1}R_1$ where $R_1$ is a hydrocarbyl group with 5-22 carbon atoms, $A_1$ is an alkyleneoxy group with 3-4 carbon atoms and $n_1$ is a number between 0-30.

2. The ortho ester surfactant of claim 1, which further contains 0-1 substituents of a non-ionic group different from $(A_1)_{n1}R_1$, and which is selected from the group consisting of an alkyl group with 1-6 carbon atoms and a hydrophilic alkyl blocked polyoxyalkylene group.

3. The ortho ester surfactant of claim 1 having the formula

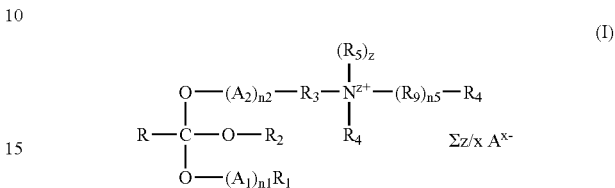

where R is hydrogen or an aliphatic group with 1-7 carbon atoms; $R_1$ is an aliphatic group with 5-22 carbon atoms; $A_1$ is an alkyleneoxy group with 3-4 carbon atoms; $A_2$ is an alkyleneoxy group with 2-3 carbon atoms where at least 50% of the alkyleneoxy groups are ethyleneoxy groups; $n_1$ is a number between 0 and 30, provided that when $R_1$ is an aliphatic group with 5-6 carbon atoms $n_1$ is at least 1; $n_2$ is a number between 0 and 30; $R_3$ is an alkylene group with 1-4 carbon atoms; z is 0 or 1 and Σz is 0-4; $n_5$ is a number 0-1; $R_5$ is an alkyl group with 1-2 carbon atoms or a group $(C_2H_4O)_sH$, where s is 1-10; $R_4$ is an alkyl group with 1-2 carbon atoms, a group $(C_2H_4O)_aH$, where a is 1-10, or the group

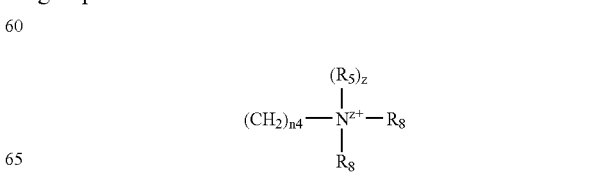

where $n_4$ is a number between 1 and 4, $R_8$ is an alkyl group with 1-2 carbon atoms or a group $(C_2H_4O)_sH$, where s is 1-10; and $R_5$ and z have the same meaning as above; $R_9$ is a group

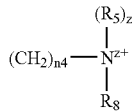

where $R_5$, $R_8$, z and $n_4$ have the same meaning as above; or the whole group

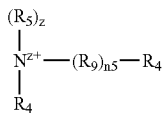

in formula I represents the group

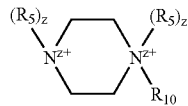

where $R_{10}$ is an alkyl group with 1-2 carbon atoms, or a group $(C_2H_4O)_sH$, where s is 1-10; and $R_5$ and z have the same meaning as above; $R_2$ is selected from the group consisting of $-(A_1)_{n1}R_1$, $-(A_2)_{n2}-R_3-N^{z+}(R_4)(R_5)_z(R_9)_{n5}-R_4$, an alkyl group with 1-6 carbon atoms, and $-(A_3)_{n3}R_6$, where A3 is an alkyleneoxy group with 2-3 carbon atoms and at least 50% of the alkyleneoxy groups are ethyleneoxy groups, $n_3$ is a number between 0-30 and $R_6$ is an alkyl group with 1-4 carbon atoms; $A_1$, $A_2$, $n_1$, $n_2$, $n_5$, $R_1$, $R_3$, $R_4$, $R_5$ and $R_9$ have the same meaning as mentioned above and $A^{x-}$ is an anion, where x is the charge of the anion; or a di- or polycondensate via any of the free hydroxy groups of the ortho ester.

4. An ortho ester surfactant according to any one of claims 1-3, where $R_1$ is an alkyl group with 8-22 carbon atoms.

5. The ortho ester surfactant of claim 4, wherein $n_1$ is a number between 0-20.

6. The ortho ester surfactant of claim 4 wherein $R_5$ is methyl.

7. A process for the preparation of an ortho ester quaternary surfactant according to claim 1 which comprises preparing a tertiary amino ortho ester by reacting a trialkyl ortho ester, where the alkyl groups contain 1-6 carbon atoms, in one or several steps, with a hydroxyl-containing tertiary amine free from hydrocarbyl groups with 5 or more carbon atoms, and with a hydroxyl compound including a hydrophobic group with the formula $R_1(A_1)_{n1}$, where $R_1$, $A_1$ and $n_1$ have the meaning mentioned in claim 1, while evaporating alcohols derived from the alkyl groups of the ortho ester, and thereafter forming said quaternary ammonium ortho ester surfactant by further reacting the tertiary amino ortho ester with an alkylating agent.

8. A process for the preparation of a quaternary ammonium ortho ester surfactant according to claim 3 which comprises preparing a tertiary amino ortho ester by reacting an ortho ester of the general formula

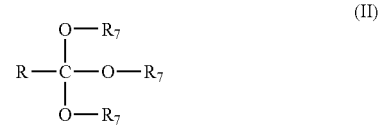

where R is hydrogen or an aliphatic group with 1-7 carbon atoms and $R_7$ is an alkyl group with 1-6 carbon atoms, in one or several steps, with reactants having the formulas HO—$(A_1)_{n1}$—$R_1$, HO—$(A_2)_2$—$R_3$—$N(R_4)(R_9)_{n5}$—$R_4$ and, if so required, HO—$(A_3)_3$—$R_6$ where $R_1$, $R_3$, $R_4$, $R_6$, $R_9$, $A_1$, $A_2$, $A_3$, $n_1$, $n_2$, $n_3$ and $n_5$ have the same meaning as in claim 3, while evaporating alcohols with the formula $R_7OH$, where $R_7$ has the same meaning as above, and further reacting the tertiary amino ortho ester obtained with an alkylating agent containing an alkyl group with 1-2 carbon atoms, or with ethylene oxide in the presence of an acid in order to obtain said quaternary ammonium ortho ester surtactant.

9. A wetting agent, hydrotrope or rheology additive which comprises the ortho ester surfactant of claim 1.

10. A disinfectant, biocide or wood preservation agent which comprises the ortho ester surfactant of claim 1.

11. A softener, anti-static additive or personal care product which comprises the ortho ester surfactant of claim 1.

12. A flotation agent, corrosion inhibitor, chain lubricant, debonding agent for cellulose pulp, or an agent in viscose processing and in fibre and textile processes which comprises the ortho ester surfactant of claim 1.

* * * * *

UNITED STATES PATENT AND TRADEMARK OFFICE
CERTIFICATE OF CORRECTION

PATENT NO. : 7,288,510 B2  
APPLICATION NO. : 10/487972  
DATED : October 30, 2007  
INVENTOR(S) : Per-Erik Hellberg Page 1 of 1

It is certified that error appears in the above-identified patent and that said Letters Patent is hereby corrected as shown below:

Cover, (57) Abstract, Line 3, change "am" to --are--.

Signed and Sealed this

Twenty-fifth Day of August, 2009

David J. Kappos
*Director of the United States Patent and Trademark Office*